(12) United States Patent
Kreeger

(10) Patent No.: US 10,146,904 B2
(45) Date of Patent: Dec. 4, 2018

(54) METHODS AND SYSTEMS AND DYNAMIC VISUALIZATION

(71) Applicant: FOVIA, INC., Palo Alto, CA (US)

(72) Inventor: Kevin Kreeger, Palo Alto, CA (US)

(73) Assignee: FOVIA, INC., Palo Alto, CA (US)

( * ) Notice: Subject to any disclaimer, the term of this patent is extended or adjusted under 35 U.S.C. 154(b) by 124 days.

(21) Appl. No.: 15/357,524

(22) Filed: Nov. 21, 2016

(65) Prior Publication Data

US 2017/0148159 A1 May 25, 2017

Related U.S. Application Data

(60) Provisional application No. 62/260,154, filed on Nov. 25, 2015.

(51) Int. Cl.
*G06F 19/00* (2018.01)
*G06T 19/00* (2011.01)

(52) U.S. Cl.
CPC ............ *G06F 19/00* (2013.01); *G06F 19/321* (2013.01); *G06T 19/00* (2013.01); *G06T 2210/41* (2013.01)

(58) Field of Classification Search
CPC ... G06T 7/0012; G06T 19/20; G06T 2200/04; G06T 2210/41; A61B 6/463; A61B 6/466; A61B 6/5217; G06F 19/34; G16H 30/40; G16H 50/20
See application file for complete search history.

(56) References Cited

U.S. PATENT DOCUMENTS

2005/0171430 A1* 8/2005 Zhang et al. ................. 600/437
2007/0100234 A1* 5/2007 Arenson et al. .............. 600/429

FOREIGN PATENT DOCUMENTS

WO WO-2014/149554 A1 * 9/2014 ............... A61B 6/02

* cited by examiner

*Primary Examiner* — Andrew W Johns
(74) *Attorney, Agent, or Firm* — Dentons US LLP

(57) ABSTRACT

Methods and systems related to dynamic visualization of a representation of a first three-dimensional (3D) object are provided. In some embodiments, a computer system receives a request for facilitating identification of the representation of the first 3D object based on a plurality of images. The plurality of images represents datasets associated with a series of slices of a second 3D object. The computer system identifies a current image of the plurality of images based on the request. The current image represents a dataset associated with a current slice of the series of slices. The computer system displays, in absence of additional user input, two or more images of the plurality of images to facilitate visualization of the representation of the first 3D object. The two or more images include the current image and one or more images representing datasets associated with neighboring slices of the current slice.

23 Claims, 5 Drawing Sheets

METHODS AND SYSTEMS AND DYNAMIC VISUALIZATION

CROSS-REFERENCE TO RELATED APPLICATIONS

This application claims priority to U.S. Provisional Patent Application Ser. No. 62/260,154, filed on Nov. 25, 2015, entitled "METHODS AND SYSTEMS FOR DYNAMIC VISUALIZATION," which is hereby incorporated by reference in its entirety for all purposes.

FIELD

The present disclosure relates generally to image processing. More particularly, the present disclosure relates to dynamic visualization of a representation of a three-dimensional (3D) object.

BACKGROUND

A radiologist may frequently need to search for, for example, a nodule (e.g., a lung nodule) using computed tomography (CT) scan images. The size of a nodule may be substantially smaller than the sizes of other structures of the object (e.g., a lung) scanned. For example, FIG. 1A illustrates an exemplary CT scan image 100 representing a dataset of a lung slice. A CT scan image represents an axial or cross-sectional image of a 3D object, such as a lung. Axial or cross-sectional images represent datasets associated with virtual slices of the 3D object. As shown in FIG. 1A, in CT scan image 100, a representation 102 of a lung nodule may appear as a small white dot or circle. However, in CT image 100, the representations of other structures of a lung may also appear as small white dots or circles. But the other structures may not be lung nodules. Rather, they may be branching airways, arteries of veins, etc. As a result, a radiologist may have difficulty visually detect the representation (e.g., representation 102) of a lung nodule using a single CT scan image (e.g., CT scan image 100).

This difficulty may be mitigated or reduced by, for example, generating a CT scan image representing a dataset associated with a thicker slice of the lung or manually navigating through multiple CT scan images. For example, FIG. 1B illustrates an exemplary CT scan image 220 representing a dataset of a lung slice having a thickness that is greater than that of the lung slice shown in FIG. 1A. With a thicker slice, non-nodule structures, such as branching airways, arteries, and veins, may appear to be longer than a dot or circle because they typically extend through the thicker slice at an angle. A nodule, on the other hand, would remain as a dot or circle in a thicker slice. As a result, a radiologist can potentially distinguish between a lung nodule and other lung structures. The thicker slice approach, however, may not be readily available or may not be efficient in visual detection of a nodule. For example, the thickness would need to be determined or optimized for better distinguishing the nodules from non-nodule structures. This may involve a cumbersome and time consuming process and may not be desired.

Moreover, a radiologist may attempt to visually detect a nodule using multiple images representing datasets of regular or thin slices of a lung. For doing that, the radiologist may need to manually navigating through multiple CT scan images. Such navigation may require, for example, scrolling the track wheel of a computer mouse up and down for a large number of times. In addition, during the scrolling, the radiologist may easily lose track of the image on which he or she is attempting to visually detect the nodule. Therefore, the approach of manual navigation through multiple CT scan images can also be cumbersome and inefficient.

SUMMARY

Methods and systems related to dynamic visualization of a representation of a first three-dimensional (3D) object are provided. In some embodiments, a computer system receives a request for facilitating identification of the representation of the first 3D object based on a plurality of images. The plurality of images represents datasets associated with a series of slices of a second 3D object. The computer system identifies a current image of the plurality of images based on the request. The current image represents a dataset associated with a current slice of the series of slices. The computer system displays, in absence of additional user input, two or more images of the plurality of images to facilitate visualization of the representation of the first 3D object. The two or more images include the current image and one or more images representing datasets associated with neighboring slices of the current slice.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise.

It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The details of one or more embodiments of the subject matter described in the specification are set forth in the accompanying drawings and the description below. Other features, aspects, and advantages of the subject matter will become apparent from the description, the drawings, and the claims.

DETAILED DESCRIPTION

The following description sets forth exemplary systems and methods for dynamic visualization of a representation of a first three-dimensional (3D) object (e.g., a target lesion). It should be recognized, however, that such description is not intended as a limitation on the scope of the present disclosure but is instead provided as a description of exemplary embodiments.

Figure 1A:
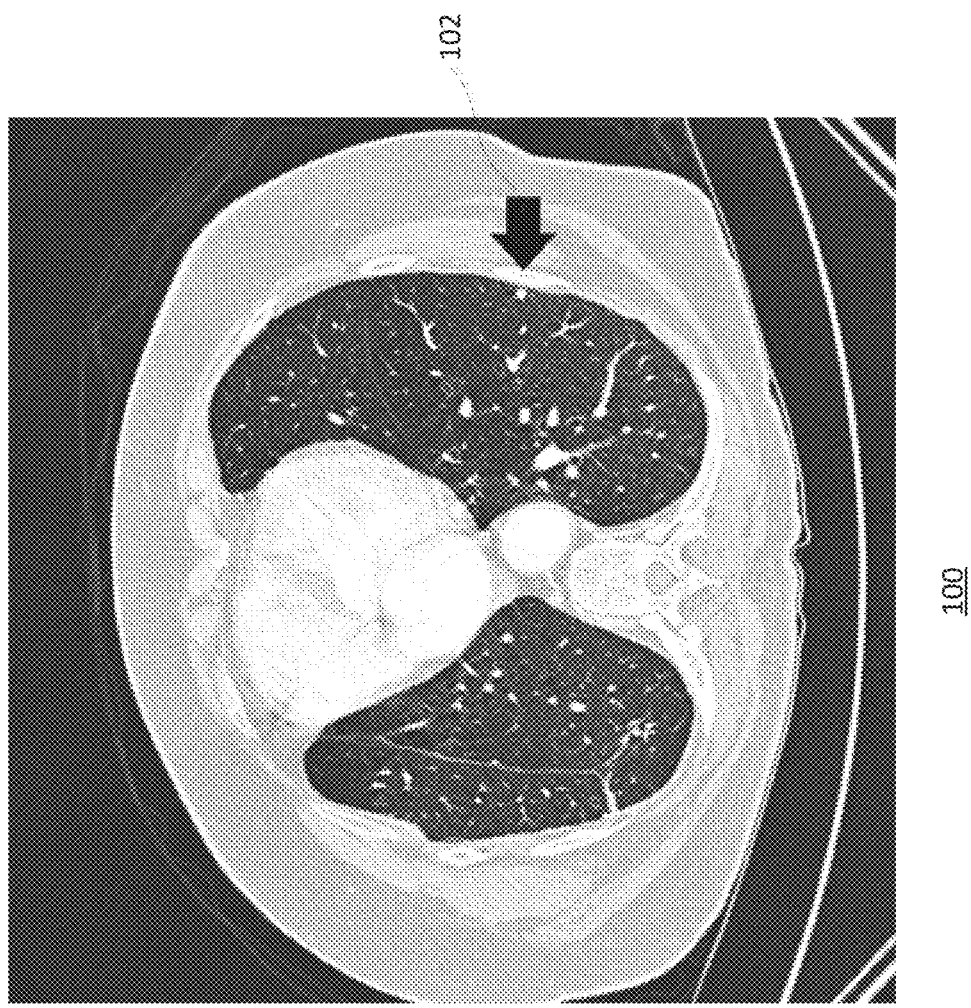
FIG. 1A illustrates an exemplary CT scan image representing a dataset of a lung slice.
Figure 1B:
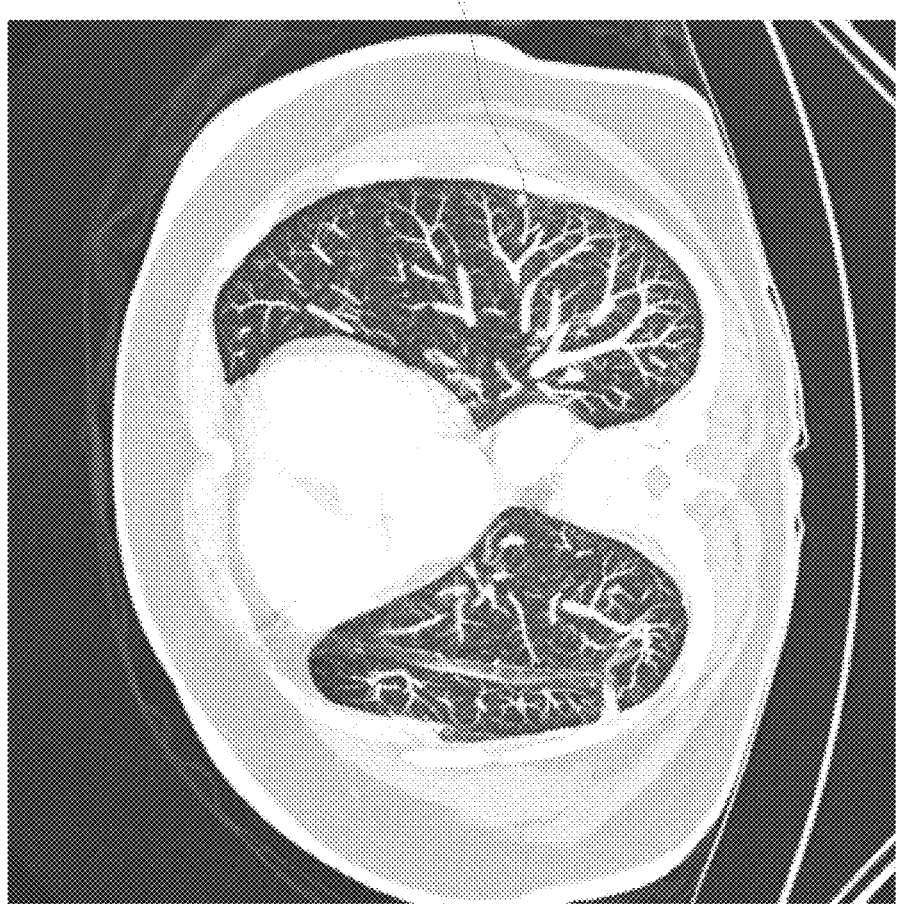
FIG. 1B illustrates an exemplary CT scan image representing a dataset of a thicker lung slice than FIG. 1A.
Figure 2:
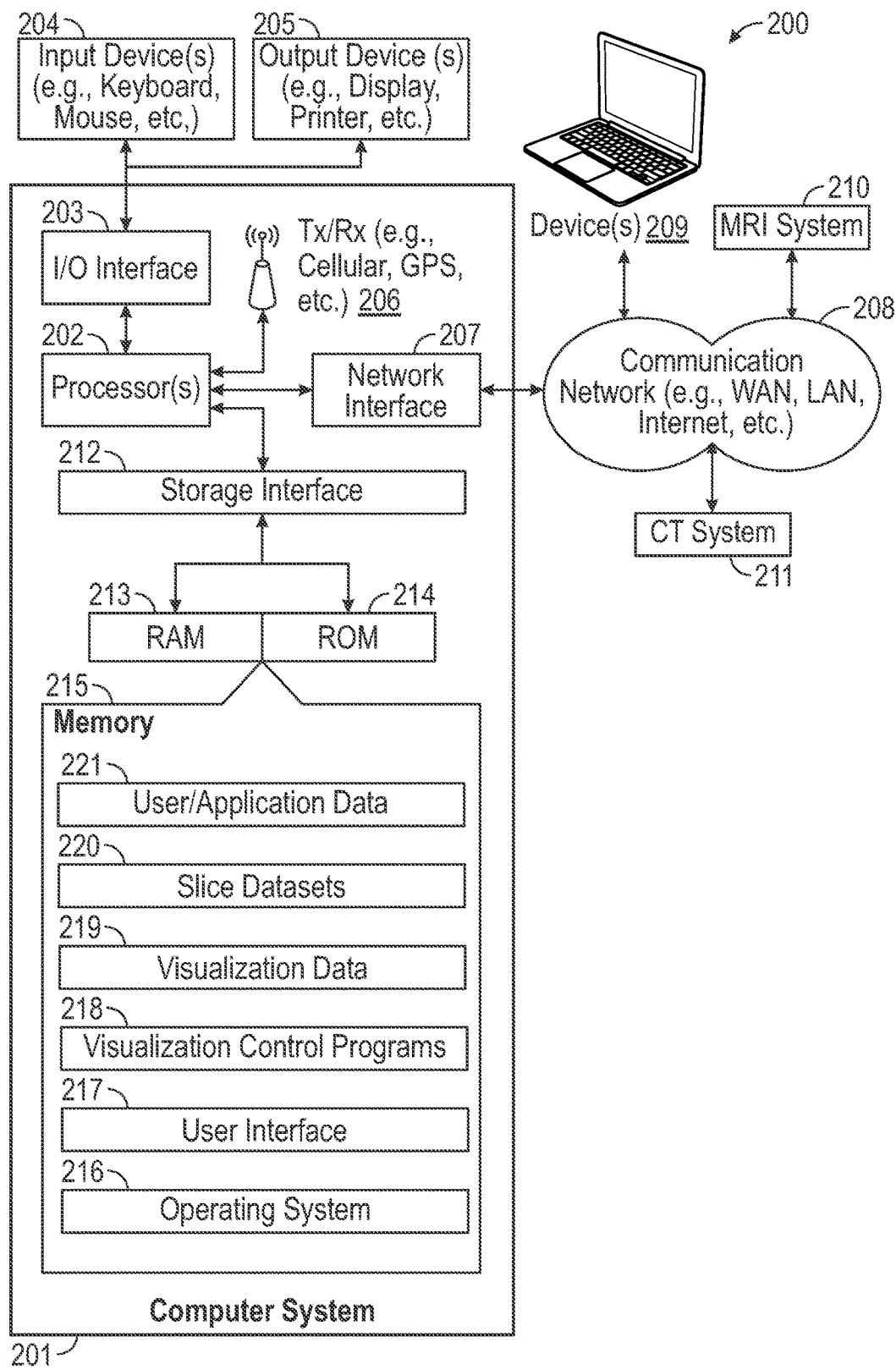
FIG. 2 illustrates an exemplary system for dynamic visualization, consistent with some embodiments of the present disclosure.

FIG. 2 illustrates an exemplary system 200 for dynamic visualization, consistent with some embodiments of the present disclosure. Dynamic visualization can include displaying two or more images in a particular manner to facilitate visualization of a representation of a first 3D object, such as a target lesion, a nodule, an abnormality of a human body, an aggregation of cells, or a tumor. The first 3D object (e.g., a lung nodule) may be a portion of a second 3D object (e.g., a lung); and may have small dimensions such that it is difficult to detect by a human visual system. In some embodiments, dynamic visualization may generate a flashing effect with respect to the representation of a small object. For example, the representation of the first 3D object may only appear in one of a plurality of images. Thus, by displaying two or more images in a particular manner (e.g., sequentially or back-and-forth rapidly), the first 3D object may appear to be flashing (e.g., appearing on one image and disappearing on other images). This kind of flashing effect may be readily detected by a human visual system or by an instrument. As a result, the representation of the first 3D object (e.g., a target lesion) can be readily detected. Dynamic visualization is described in more detail below.

Referring to FIG. 2, system 200 may include a computer system 201, input devices 204, output devices 205, devices 209, Magnet Resonance Imaging (MRI) system 210, and Computed Tomography (CT) system 211. It is appreciated that one or more components of system 200 can be separate systems or can be integrated systems. In some embodiments, computer system 201 may comprise one or more central processing units ("CPU" or "processor(s)") 202. Processor(s) 202 may comprise at least one data processor for executing program components for executing user- or system-generated requests. A user may include a person, a person using a device such as those included in this disclosure, or such a device itself. The processor may include specialized processing units such as integrated system (bus) controllers, memory management control units, floating point units, graphics processing units, digital signal processing units, etc. The processor may include a microprocessor, such as AMD Athlon, Duron or Opteron, ARM's application, embedded or secure processors, IBM PowerPC, Intel's Core, Itanium, Xeon, Celeron or other line of processors, etc. The processor 202 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor(s) 202 may be disposed in communication with one or more input/output (I/O) devices via I/O interface 203. I/O interface 203 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using I/O interface 203, computer system 201 may communicate with one or more I/O devices. For example, input device 204 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, electrical pointing devices, etc. Output device 205 may be a printer, fax machine, video display (e.g., cathode ray tube (CRT), liquid crystal display (LCD), light-emitting diode (LED), plasma, or the like), audio speaker, etc. In some embodiments, a transceiver 206 may be disposed in connection with the processor(s) 202. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, processor(s) 202 may be disposed in communication with a communication network 208 via a network interface 207. Network interface 207 may communicate with communication network 208. Network interface 207 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. Communication network 208 may include, without limitation, a direct interconnection, local area network (LAN), wide area network (WAN), wireless network (e.g., using Wireless Application Protocol), the Internet, etc. Using network interface 207 and communication network 208, computer system 201 may communicate with devices 209. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, computer system 201 may itself embody one or more of these devices.

In some embodiments, using network interface 207 and communication network 208, computer system 201 may communicate with MRI system 210, CT system 211, or any other medical imaging systems. Computer system 201 may communicate with these imaging systems to obtain images for dynamic visualization. Computer system 201 may also be integrated with these imaging systems.

In some embodiments, processor 202 may be disposed in communication with one or more memory devices (e.g., RAM 213, ROM 214, etc.) via a storage interface 212. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, flash devices, solid-state drives, etc.

The memory devices may store a collection of program or database components, including, without limitation, an operating system 216, user interface 217, visualization control program 218, visualization data 219, slice datasets 220, user/application data 221 (e.g., any data variables or data records discussed in this disclosure), etc. Operating system 216 may facilitate resource management and operation of computer system 201. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 217 may facilitate display, execution, interaction, manipulation, or operation of program components through textual or graphical facilities. For example, user interfaces may provide computer interaction interface elements on a display system operatively connected to computer system 201, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, computer system 201 may implement visualization control program 218 for controlling the manner of displaying a plurality of images to facilitate the identification of a representation of a first 3D object. In some embodiments, computer system 201 can implement visualization control program 218 such that the images are displayed sequentially, repeatedly, recursively, reciprocally, upwardly, downwardly, randomly, selectively, or in any combination thereof. For example, visualization control program 218 can identify and store the identification of a plurality of images (e.g., the identification numbers or names of images) and generate a sequence or an order of displaying the plurality of images based on a request and/or based on default setting. In some embodiments, the plurality of images can represent the datasets associated with a series of slices of a second 3D object (e.g., slice datasets 220). In some embodiments, the sequence or order of the image displaying may be stored as visualization data 219. In some embodiments, visualization control program 218 can include a randomize algorithm to generate a random sequence for displaying the images.

In some embodiments, computer system 201 may store user/application data 221, such as data, variables, and parameters (e.g., one or more parameters for controlling the displaying of images) as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of any computer or database component may be combined, consolidated, or distributed in any working combination.

Disclosed embodiments describe systems and methods for dynamic visualization. The illustrated components and steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items.

Figure 3:
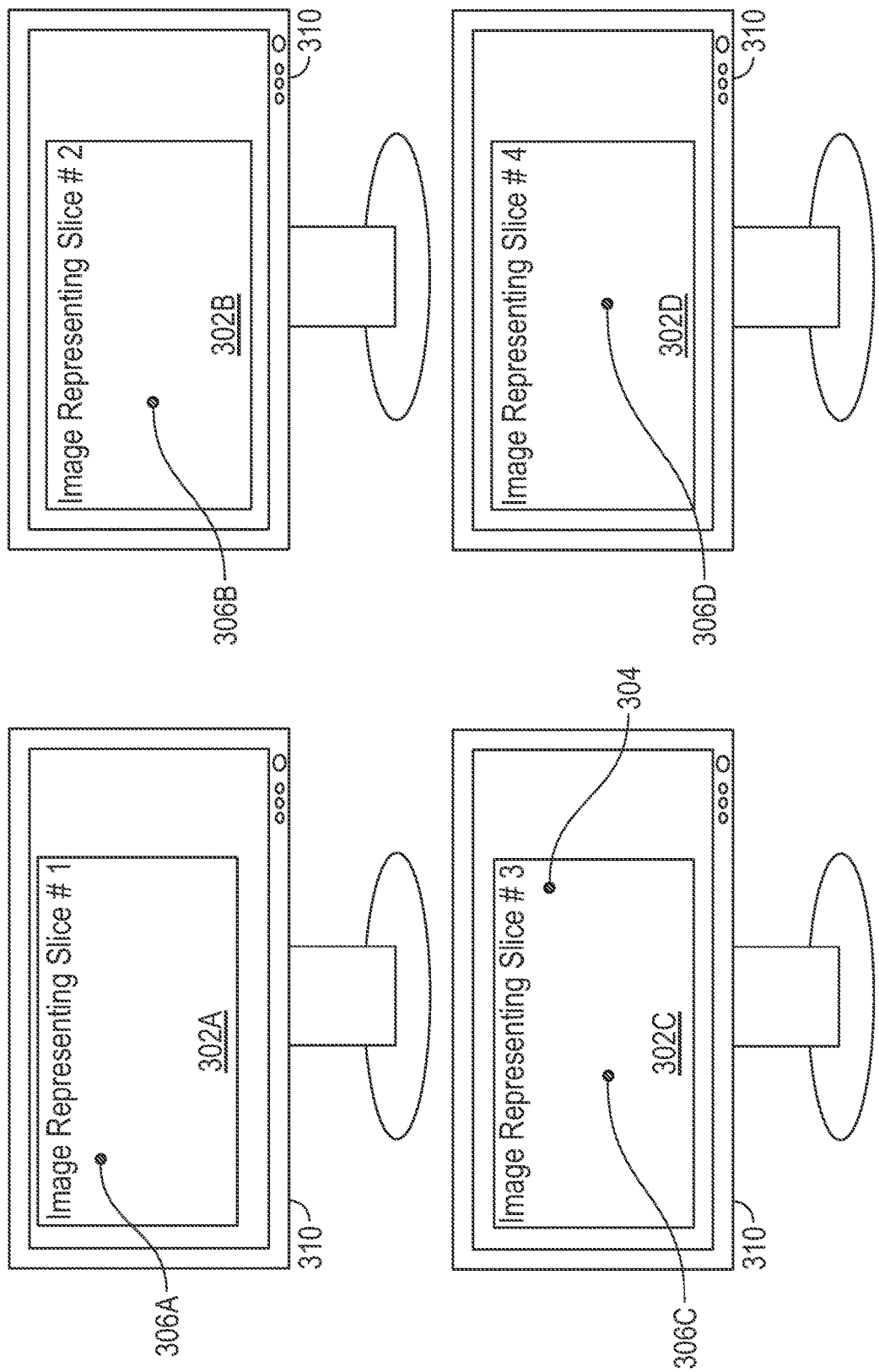
FIG. 3 illustrates exemplary images for facilitating identification of a representation of a first 3D object, consistent with some embodiments of the present disclosure.

FIG. 3 illustrates exemplary images 302A-D for facilitating identification of a representation of a first 3D object, consistent with some embodiments of the present disclosure. A first 3D object (e.g., a lung nodule) can be a portion of a second 3D object (e.g., a lung). The first 3D object may be, for example, a target lesion, an abnormality of a human body, an aggregation of cells, a nodule, a tumor, or a combination thereof. The second 3D object may be a portion of a human body, a portion of an animal body, or a lifeless object. In some embodiments, the size of the first 3D object is smaller than the size of the second 3D object. As discussed above, one or more axial or cross-sectional images can be generated with respect to the second 3D object. For example, a CT system (e.g., CT system 211) can generate CT scan images of the second 3D object (e.g., a lung). The CT scan images are axial or cross-sectional images representing datasets associated with virtual slices (referred as "slices" hereinafter) of the second 3D object. The slices may have any desired dimensions. For example, the slices may an average of 5 mm thickness or a near-zero thickness. They may also have the same thicknesses or different thicknesses.

In some embodiments, a CT system may generate a series of images representing datasets associated with consecutive or neighboring slices of the second 3D object. For example, referring to FIG. 3, images 302A-D may represent datasets associated with consecutive or neighboring slices (e.g., slices #1-4) of a the second 3D object (e.g., a lung). Neighboring slices may or may not be consecutive or immediately adjacent to each other. For example, slice #1 and slice #3 may be neighboring slices and may not be consecutive slides. In some embodiments, the representation (e.g., a dot or a circle) of a first 3D object (e.g., a target lesion) may appear on images representing one or more slices of the second 3D object, but not on other slices. For example, a dot or circle representing a lung nodule may appear only on image 302C representing slice #3 generated by a CT scan, but may not appear on images 302A, B, and D representing slice #1, 2, and 4, respectively.

As discussed above, a first 3D object (e.g., a lung nodule) may be part of a second 3D object (e.g., a lung); and may have small dimensions. As a result, detecting the representation of the first 3D object on an image (e.g., a CT scan image) may be difficult. In some embodiments, dynamic visualization can be used to facilitate detecting of the representation of the first 3D object. Dynamic visualization can generate a flashing effect with respect to the representation of the first 3D object. For example, referring to FIG. 3, the representation of the first 3D object may only appear in one of the images (e.g., image 302C representing slice #3). Thus, by displaying two or more images representing the neighboring slices in a particular manner (e.g., sequentially or rapidly up and down), the representation of the first 3D object may appear to be flashing (e.g., it appears on one image and disappears on other images). This kind of flashing effect may be readily detected by a human visual system or by an instrument (e.g., a camera). As a result, the representation of the first 3D object can be readily detected.

Referring to FIG. 3, for example, the representation of the first 3D object (e.g., representation 304) may only appear on image 302C, and not on other images 302A, B, or D. As a result, a computer system (e.g., computer system 201) can display images 302A-D in a particular manner to generate a flashing effect with respect to representation 304. For example, the computer system can display image 302C first, followed by displaying images 302B, 302A, 302B, 302C, and 302D at the same or similar screen location where image 302C is displayed (e.g., at the same or similar screen location of display 310). Displaying the images in such an order may generate an animation and/or a flashing effect with respect to representation 304. The flashing effect is generated because representation 304 appears on the screen while image 302C is being displayed and disappears while other images are being displayed. It is appreciated that the computer system can display images 302A-D in any desired manner for facilitating the identification of the representation of the first 3D object (e.g., representation 304). For example, the computer system can display one or more of images 302A-D sequentially, repeatedly, recursively, reciprocally, upwardly, downwardly, randomly, selectively, rapidly, or in a combination thereof. Moreover, the computer system can display any combination of neighboring images. For example, the computer system may display 302A and 302C, but not 302B and 302D.

Referring to FIG. 3, an image representing a slice may also include representations of one or more third 3D objects. The third 3D objects (e.g., structures such as branching airways or veins) may be a portion of the second 3D object (e.g., a lung) and can be different from the first 3D object (e.g., a lung nodule). The third 3D object may have dimensions greater that those of the first 3D object. For example, a branching airway may have a greater longitudinal dimension than a lung nodule.

The representations of some third 3D objects may have similar shapes and/or dimensions on the image as that of the representation of the first 3D object. For example, as shown in FIG. 3, a representation of a branching airway (e.g., representation 306C) may have a similar shape (e.g., a dot or a circle) and dimension as those of a representation of a lung nodule (e.g., representation 304). In some embodiments, dynamic visualization can facilitate distinguishing the representation of a first 3D object from the representation of the third 3D object. As discussed above, dynamic visualization can generate a flashing effect with respect to the representation of a first 3D object. Dynamic visualization can also generate a shifting or moving effect with respect to the representation of a third 3D object.

For example, a first 3D object may be a lung nodule and a third 3D object may be a branching airway. Correspondingly, as shown in FIG. 3, a cross-sectional image of the branching airway may be represented as a dot or circle (e.g., representation 306C) similar to the representation of a lung nodule (e.g., representation 304). As a result, on image 302C, representation 306C may appear to have a shape and dimensions similar to those of the representation 304. Without dynamic visualization, it may be difficult to distinguish representation 304 from representation 306C.

In some embodiments, a computer system (e.g., computer system 201) can generate a shifting or moving effect with respect to representation 306. Similar to generating the flashing effect, the computer system can display image 302C first, followed by displaying images 302B, 302A, 302B, 302C, and 302D at the same or similar screen location. Besides generating a flashing effect with respect to representation 304, as discussed above, displaying images in such an order may also generate a moving or shifting effect with respect to representation 306C.

For example, representation 306C is a representation of a cross-sectional image of a branching airway. The branching airway is typically longer than the dimension of a lung nodule, Thus, unlike the long nodule, which may be represented only on image 302C, the branching airway may have multiple representations 306A-D on multiple images 302A-D representing multiple corresponding slices. Each of these representations 306A-D may show a cross-section at a corresponding location along the longitudinal direction of the branching airway. In some embodiments, while the branching airway may have multiple representations 306A-D, the multiple representations 306A-D may not be displayed at the same corresponding locations of images 302A-D. For example, the branching airway may extend from the upper left to the lower right of a lung. Due to such extension of the branching airway, representation 306A may have a location that is more toward the upper left of image 302A than the location of representation 306B displayed on image 302B; and representation 306B may have a location that is more towards the upper left of image 302B than the location of representation 306C displayed on image 302C, and so forth. As a result, by displaying images 302A-D in a particular manner (e.g., displaying them at the same screen location up and down rapidly), the computer system can generate a moving or shifting effect because representations 306A-D of the third 3D object appear at different locations of the images 302A-D. It is appreciated that the computer system can display images 302A-D in any desired manner. For example, the computer system may display images 302A-D sequentially, repeatedly, recursively, reciprocally, upwardly, downwardly, randomly, selectively, rapidly, or in a combination thereof. Moreover, the computer system may display any number of images 302A-D. For example, the computer system may display images 302A and 302C, but not 302B and 302D.

Referring to FIG. 3, displaying multiple images (e.g., images 302A-D) in a particular manner can generate a flashing effect with respect to the representation of a first 3D object (e.g., a lung nodule) and a moving or shifting effect with respect to the representation of a third 3D object (e.g., a branching airway). Thus, the representation of the first 3D object (e.g., representation 304) can be readily distinguished from the representation of third 3D object (e.g., representation 306C). As a result, the computer system can provide dynamic visualization to facilitate identification of the representation of the first 3D object.

In some embodiments, the computer system can also display a plurality of images (e.g., images 302A-D) to facilitate identification of the first 3D object according to one or more visualization parameters. These visualization parameters can include, for example, a manner of displaying the images, a time period for displaying each image, a rate of displaying, a number of images to be displayed, and a distribution of the images to be displayed. The manner of displaying the images can include, for example, displaying sequentially, repeatedly, recursively, reciprocally, upwardly, downwardly, randomly, selectively, rapidly, or in a combination thereof. The time period for displaying each image can be configured to enable or enhance the identification of the representation of the first 3D object. For example, the time period for displaying each image may be on the order of microseconds, milliseconds, a fraction of a second, or seconds. In some embodiments, the time period for displaying each image can be the same or different.

In some embodiments, the rate of displaying can also be configured to enable or enhance the identification of the representation of the first 3D object. For example, the rate of displaying may indicate a speed for displaying (e.g., displaying 2 images per millisecond or second), or may indicate a time gap between displaying two images (e.g., a time gap of 10 milliseconds). It is appreciated that the rate of displaying can have any desired value for enhancing or optimizing the identification of the representation of the first 3D object.

In some embodiments, the number of images to be displayed and the distribution of the images to be displayed can also be configured. For example, the total number of images to be displayed may be configured or optimized to be 4, 6, 8, 10, etc., for enhancing or optimizing the identification. The distribution of the images to be displayed provides at least one of the number of images preceding a current image and the number of images following the current image. The current image can be an image that the user is examining or desired to examine. For example, referring to FIG. 3, the current image may be image 302C representing slice #3. The distribution of the images may provide that two images preceding image 302C (i.e., images 302A and 302B) and one image following image 302C (i.e., image 302D) are to be displayed. In some embodiments, the distribution of the image can also indicate which of the neighboring images are to be displayed. For example, referring to FIG. 3, the distribution of images may indicate that image 302A, 302C, and 302D are displayed, but not 302B.

In some embodiments, one or more of visualization parameters, such as the time period for displaying each image, the rate of displaying, the number of images to be displayed, and the distribution of the images to be displayed, can be configured or optimized to be within corresponding ranges sufficient for enabling identification of the representation of the first 3D object. For example, the number of images may be configured such that it is sufficient to enable the user to distinguish a first 3D object (e.g., a lung nodule) from a third 3D object (e.g., a branching airway). The computer system may start with some number (e.g., two images) of images. If it is determined that the first 3D object cannot be detected or distinguished with displaying the two images, the computer system may reconfigure to increase the number (e.g., 4 images) to be displayed. The computer system may reconfigure the visualization parameters as many times as desired.

In some embodiments, the computer system can obtain the visualization parameters from a user, a database, and/or use default configurations. For example, the computer system can provide a user interface (e.g., user interface 217) for obtaining user inputs of one or more visualization parameters. The computer system can also store previously obtained visualization parameters in a database (e.g., visualization data 219) of memory 215, RAM 213, Rom 214, and/or any other storage devices. By storing the visualization parameters, the computer system enables re-using of the same or similar sets of visualization parameters for the next dynamic visualization of a representation of a first 3D object. For example, for identification of an additional or a new first 3D object, the computer system may allow retrieving and/or reloading of visualization parameters that are previously used or provided. In some embodiments, the computer system can determine or detect that no user input is provided with respect to the visualization parameters. The computer system can thus use a default setting or configuration for the next dynamic visualization.

Figure 4:
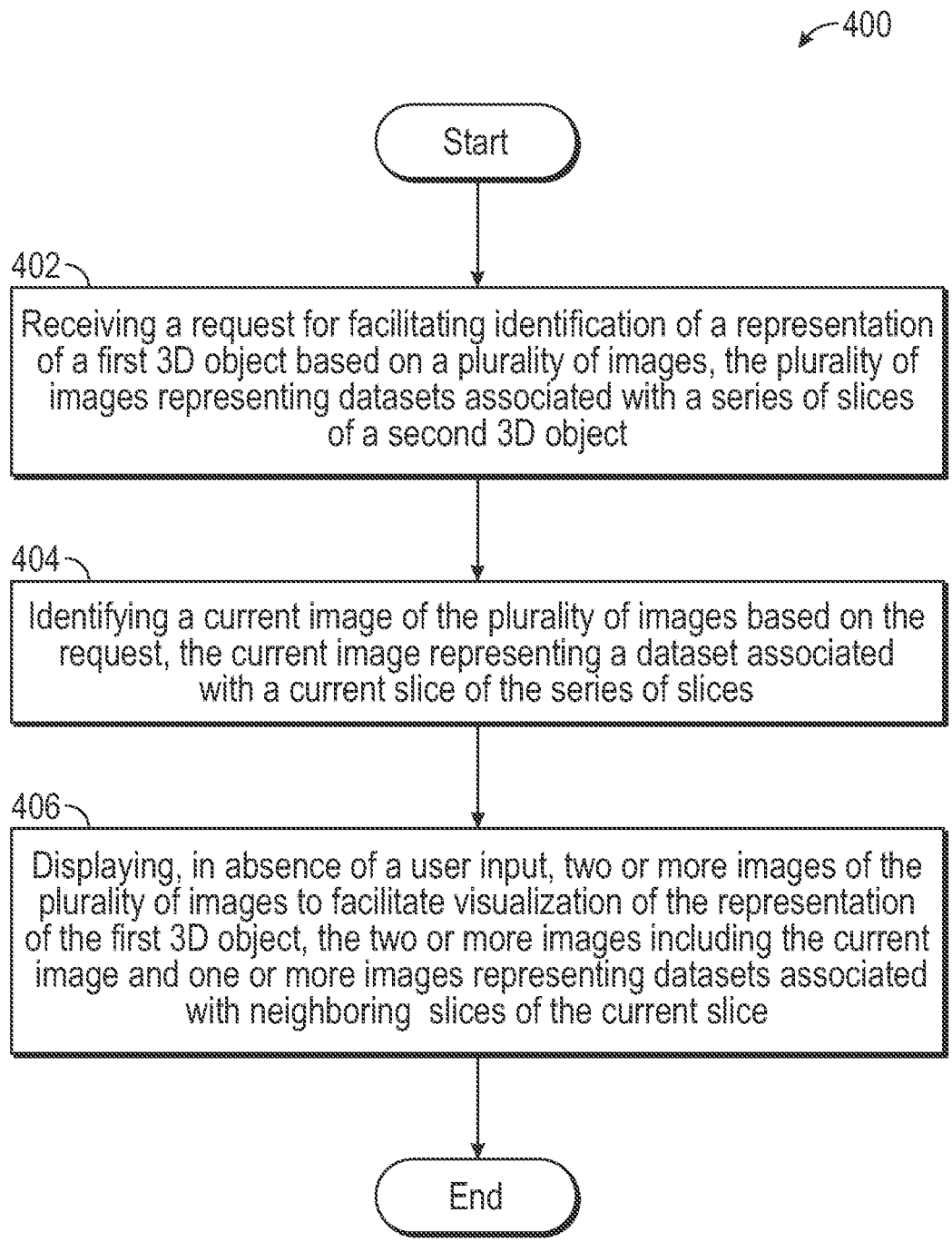
FIG. 4 illustrates a flow chart of an exemplary process for dynamic visualization, consistent with some embodiments of the present disclosure.

FIG. 4 illustrates a flow chart of an exemplary process 400 for dynamic visualization of a representation of a first 3D object, consistent with some embodiments of the present disclosure.

In process 400, a computer system (e.g., computer system 201) can receive (step 402) a request for facilitating identification of the representation of the first 3D object based on a plurality of images. The request may be provided by a user, such as a radiologist, or by another system such as CT system 211. The computer system can receive the request using a user interface (e.g., user interface 217). In some embodiments, the request can be associated with one or more of: an instruction for displaying the two or more images, an identification of the current image, and one or more parameters for controlling the displaying of the two or more images. For example, the request may include an instruction to display the plurality of images in a particular manner. The request may also provide an identification of a current image (e.g., image 302C shown in FIG. 3). The current image can be an image that the user is currently examining or visualizing. For example, the current image may be an image that a radiologist is examining to identify a possible target lesion such as a lung nodule. The identification of the current image may uniquely identify the current image. For example, the identification can be the image identification number or the image name.

In some embodiments, the request can also be associated with one or more visualization parameters. As discussed above, the visualization parameters can include, for example, a manner of displaying the images, a time period for displaying each image, a rate of displaying, a number of images to be displayed, and a distribution of the images to be displayed. In some embodiments, the computer system can store the request, the instruction for displaying the two or more images, the identification of the current image, and/or the visualization parameters in a storage (e.g., storing visualization data 219 and/or user/application data 221 in memory 215, RAM 213, ROM 214, or any other storage devices).

In some embodiments, the first 3D object can be a visual representation of at least one of: a target lesion, an abnormality of a human body, an aggregation of cells, a nodule, and a tumor. The plurality of images can represent datasets associated with a series of slices of a second 3D object, such as a portion of a human body, a portion of an animal body, or a lifeless object. The series of slice may comprise, for example, two or more CT scan slices. The slices can also be referred to as virtual slices representing cross-sectional or axial images of the second 3D object.

Referring to FIG. 4, in process 400, the computer system can identify (step 404) a current image of the plurality of images based on the request. For example, the computer system can identify the current image based on an identification number of the image, a name of the image, or whether a particular image is being currently displayed on an output device (e.g., display 310). As discussed above, the computer system may receive the identification of the current image from a user and/or from another system (e.g., CT system 211). In some embodiments, the computer system may also identify the current image as the image that is currently being displayed on the screen. If a particular image is currently being displayed, the computer system may determine that the user is currently examining this particular image and thus it is the current image.

The current image can represent a dataset associated with a current slice of the series of slices of the second 3D object (e.g., a lung). For example, as shown in FIG. 3, the current image can be image 302C representing slice #3. Slice #3 is thus a current slice that is being examined among a series of slices (e.g., slices #1-4). The slices may be, for example, CT scan slices.

In some embodiments, after the computer system identifies the current image, it can track the current image. For example, the computer system can store the identification of the current image as visualization data 219 in memory 215 for subsequent use. Tracking of the current image may be desired as the computer system displays multiple images for identification of the representation of a first 3D object. For example, after the computer system displays multiple images for identification of the representation of a first 3D object, the computer system may need to stop navigating through the images and may need to return to the current image. This allows the user to further examine the current image to identify the representation of the first 3D object (e.g., a target lesion) based on the flashing effect generated by displaying multiple images in a particular manner (e.g., sequentially, repeatedly, etc.).

Referring to FIG. 4, in process 400, the computer system can display (step 406), in absence of a user input, two or more images of the plurality of images to facilitate visualization of the representation of the first 3D object. The two or more images include the current image that is identified in step 404 and one or more images representing datasets associated with neighboring slices of the current slice. In some embodiments, the computer system can display two or more images, including the identified current image, in a particular manner, such as sequentially, repeatedly, recursively, reciprocally, upwardly, downwardly, randomly, selectively, rapidly, or in a combination thereof. As discussed above, displaying two or more images in a particular manner can generate a flashing effect with respect to the representation of a first 3D object (e.g., a lung nodule) and a moving or shifting effect with respect to the representation of a third 3D object (e.g., a branching airway of a lung).

In some embodiments, after receiving the request (step 402) and identifying (step 404) the current image, the computer system can display (step 406) the two or more images automatically without additional user input or control. For example, referring to FIG. 3, the computer system can automatically display or navigate through images 302A-D without the user having to scroll up and down, or woggle, using an input device such as a computer mouse. As a result, the effort of the user for identifying the first 3D object (e.g., a target lesion such as a lung nodule) may be substantially reduced. The user may not need to focus on navigating through the images, which can be cumbersome and can cause fatigues if the user needs to navigate through a large number of images and/or a large number of times. Instead, the user can focus more on identifying the first 3D object using for example, the flashing effect and/or the moving effect.

Moreover, in some embodiments, while the computer system reduces the effort for the user by automatically navigating through the images, the computer system can still allow the user to have certain level of control of the process for dynamic visualization. As discussed above, for example, the computer system can receive a request for facilitating identification of the representation of the first 3D object. The request can be associated with one or more visualization parameters for controlling the displaying of images. Thus, by obtaining the visualization parameters, the computer system allows the user to retain control on, for example, the total number of the images such that the computer system navigates through all images as the user desires. It is appreciated that the computer system can allow the user to retain control over the dynamic visualization process by obtaining any visualization parameters as described above.

FIG. 4 is merely illustrative of a method for dynamic visualization. The illustrative discussions above are not intended to be exhaustive or to limit the invention to the precise form disclosed. Many modifications and variations are possible in view of the above teachings.

Further, the illustrated dynamic visualization methods (e.g., the process 400) described in the present disclosure enable a more efficient and effective identification of a representation of a first 3D object (e.g., a target lesion). Some of the prior visualization methods may require the user to be heavily involved in navigating through the images and thus is more prone to error and less effective. The illustrated dynamic visualization methods can provide automatic navigating to generate flashing effects for a more effective identification. As a result, the user can more effectively and accurately identify first 3D objects (e.g., long nodules). Moreover, besides improving the effectiveness and accuracy of identification, the illustrated dynamic visualization methods also provide flexible user control.

It should be noted that, despite references to particular computing paradigms and software tools herein, the computer program instructions with which embodiments of the present subject matter may be implemented may correspond to any of a wide variety of programming languages, software tools and data formats, and be stored in any type of volatile or nonvolatile, non-transitory computer-readable storage medium or memory device, and may be executed according to a variety of computing models including, for example, a client/server model, a peer-to-peer model, on a stand-alone computing device, or according to a distributed computing model in which various of the functionalities may be effected or employed at different locations. In addition, references to particular algorithms herein are merely by way of examples. Suitable alternatives or those later developed known to those of skill in the art may be employed without departing from the scope of the subject matter in the present disclosure.

It will be understood that, although the terms "first," "second," etc. may be used herein to describe various elements, these elements should not be limited by these terms. These terms are only used to distinguish one element from another. For example, a first 3D object could be termed a second 3D object, and, similarly, a second 3D object could be termed a first 3D object, without changing the meaning of the description, so long as all occurrences of the "first 3D object" are renamed consistently and all occurrences of the "second 3D object" are renamed consistently. The first 3D object and the second 3D object are both 3D objects, but they are not the same 3D objects.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects. Rather, the scope of this disclosure should be determined with reference to the appended claims.

The invention claimed is:

1. A computer-implemented method for dynamic visualization of a representation of a first three-dimensional (3D) object, comprising:
at a computer system including one or more processors and memory,
receiving a request for facilitating identification of the representation of the first 3D object based on a plurality of images, the plurality of images representing datasets associated with a series of slices of a second 3D object;
identifying a current image of the plurality of images based on the request, the current image representing a dataset associated with a current slice of the series of slices; and
displaying, in absence of additional user input, two or more images of the plurality of images to facilitate visualization of the representation of the first 3D object, the two or more images including the current image and one or more images representing datasets associated with neighboring slices of the current slice, wherein displaying of the two or more images generates a flashing effect with respect to the representation of the first 3D object.

2. The method of claim 1, wherein the first 3D object is a portion of a second 3D object, the second 3D object being a portion of a human body, a portion of an animal body, or a lifeless object.

3. The method of claim 1, wherein the representation of the first 3D object is a visual representation of at least one of: a target lesion, an abnormality of a human body, an aggregation of cells, a nodule, and a tumor.

4. The method of claim 1, wherein the request for facilitating identification is associated with at least one of: an instruction for displaying the two or more images, an identification of the current image, and one or more parameters for controlling the displaying of the two or more images.

5. The method of claim 4, wherein the one or more parameters for controlling the displaying of the two or more images include at least one of: a manner of displaying the two or more images, a time period for displaying each image, a rate of displaying, a number of images to be displayed, and a distribution of the images to be displayed.

6. The method of claim 5, wherein the manner of displaying the two or more images includes displaying the images sequentially, repeatedly, recursively, reciprocally, upwardly, downwardly, randomly, selectively, or in a combination thereof.

7. The method of claim 5, wherein at least one of the time period for displaying each image, the rate of displaying, the number of images to be displayed, and the distribution of the images to be displayed is within corresponding ranges sufficient for enabling identification of the representation of the first 3D object.

8. The method of claim 5, wherein the distribution of the images provides at least one of the number of images preceding the current image and the number of images following the current image.

9. The method of claim 1, wherein the series of slices comprises two or more computed tomography (CT) scan slices.

10. The method of claim 1, further comprising tracking the current image based on the identification of the current image of the plurality of images.

11. The method of claim 1, wherein displaying of the two or more images generates a shifting effect with respect to the representation of one or more third 3D objects.

12. A non-transitory computer readable medium having instructions stored thereon, the instructions, when executed by one or more processors of a computer system, cause the computer system to:
receive a request for facilitating identification of the representation of the first 3D object based on a plurality of images, the plurality of images representing datasets associated with a series of slices of a second 3D object;
identify a current image of the plurality of images based on the request, the current image representing a dataset associated with a current slice of the series of slices; and
display, in absence of additional user input, two or more images of the plurality of images to facilitate visualization of the representation of the first 3D object, the two or more images including the current image and one or more images representing datasets associated with neighboring slices of the current slice, wherein display of the two or more images generates a flashing effect with respect to the representation of the first 3D object.

13. A system for dynamic visualization of a representation of a first three-dimensional (3D) object, comprising:
one or more processors; and
memory having instructions stored thereon, the instruction, when executed by the one or more processors, cause the computer system to:
receive a request for facilitating identification of the representation of the first 3D object based on a plurality of images, the plurality of images representing datasets associated with a series of slices of a second 3D object;
identify a current image of the plurality of images based on the request, the current image representing a dataset associated with a current slice of the series of slices; and
display, in absence of additional user input, two or more images of the plurality of images to facilitate visualization of the representation of the first 3D object, the two or more images including the current image and one or more images representing datasets associated with neighboring slices of the current slice, wherein display of the two or more images generates a flashing effect with respect to the representation of the first 3D object.

14. A computer-implemented method for dynamic visualization of a representation of a first three-dimensional (3D) object, comprising:
at a computer system including one or more processors and memory,
receiving a request for facilitating identification of the representation of the first 3D object based on a plurality of images, the plurality of images representing datasets associated with a series of slices of a second 3D object;
identifying a current image of the plurality of images based on the request, the current image representing a dataset associated with a current slice of the series of slices; and
displaying, in absence of additional user input, two or more images of the plurality of images to facilitate visualization of the representation of the first 3D object, the two or more images including the current image and one or more images representing datasets associated with neighboring slices of the current slice, wherein displaying of the two or more images generates a shifting effect with respect to the representation of one or more third 3D objects.

15. The method of claim 14, wherein the first 3D object is a portion of a second 3D object, the second 3D object being a portion of a human body, a portion of an animal body, or a lifeless object.

16. The method of claim 14, wherein the representation of the first 3D object is a visual representation of at least one of: a target lesion, an abnormality of a human body, an aggregation of cells, a nodule, and a tumor.

17. The method of claim 14, wherein the request for facilitating identification is associated with at least one of: an instruction for displaying the two or more images, an identification of the current image, and one or more parameters for controlling the displaying of the two or more images.

18. The method of claim 17, wherein the one or more parameters for controlling the displaying of the two or more images include at least one of: a manner of displaying the two or more images, a time period for displaying each image, a rate of displaying, a number of images to be displayed, and a distribution of the images to be displayed.

19. The method of claim 18, wherein the manner of displaying the two or more images includes displaying the images sequentially, repeatedly, recursively, reciprocally, upwardly, downwardly, randomly, selectively, or in a combination thereof.

20. The method of claim 18, wherein at least one of the time period for displaying each image, the rate of displaying, the number of images to be displayed, and the distribution of the images to be displayed is within corresponding ranges sufficient for enabling identification of the representation of the first 3D object.

21. The method of claim 18, wherein the distribution of the images provides at least one of the number of images preceding the current image and the number of images following the current image.

22. The method of claim 14, wherein the series of slices comprises two or more computed tomography (CT) scan slices.

23. The method of claim 14, further comprising tracking the current image based on the identification of the current image of the plurality of images.

* * * * *